United States Patent [19]

Sezi et al.

[11] Patent Number: 5,750,711
[45] Date of Patent: May 12, 1998

[54] DICARBOXYLIC ACID DERIVATIVES

[75] Inventors: Racai Sezi; Hellmut Ahne, both of Röttenbach; Eberhard Kuehn, Hemhofen, all of Germany

[73] Assignee: Siemens Aktiengesellschaft, München, Germany

[21] Appl. No.: 704,213

[22] Filed: Aug. 28, 1996

[30] Foreign Application Priority Data

Aug. 31, 1995 [DE] Germany ............... 195 32 138.3

[51] Int. Cl.⁶ ............... C07C 231/10; C07C 381/10; C07C 67/08; C08G 63/16
[52] U.S. Cl. ............... 548/165; 548/221; 548/259; 548/542; 549/285; 560/9; 560/17; 560/23; 560/44; 560/84; 560/85; 560/86; 560/87; 560/88; 560/95; 560/98; 564/139; 528/176; 528/182; 528/208; 528/335
[58] Field of Search ............... 528/176, 182, 528/184, 208, 335; 560/9, 17, 18, 21, 22, 23, 44, 84, 88, 95, 98; 564/139; 548/165, 221, 259, 542; 549/285

[56] References Cited

U.S. PATENT DOCUMENTS

| | | |
|---|---|---|
| 4,331,592 | 5/1982 | Wissmann et al. |
| 4,339,521 | 7/1982 | Ahne et al. |
| 4,622,285 | 11/1986 | Ahne |
| 4,849,051 | 7/1989 | Ahne et al. |
| 5,021,320 | 6/1991 | Mueller et al. |
| 5,037,720 | 8/1991 | Khanna |
| 5,096,999 | 3/1992 | Hellmut et al. |
| 5,194,568 | 3/1993 | Gregory et al. |
| 5,219,981 | 6/1993 | Gregory et al. |

FOREIGN PATENT DOCUMENTS

| | | |
|---|---|---|
| 0 391 196 | 10/1990 | European Pat. Off. |
| 1393740 | 5/1975 | United Kingdom |

OTHER PUBLICATIONS

Labadie, et al., "Recent Advances in High Temperature Polymers For Microelectronic Applications", *SAMPE Journal*, vol. 25, No. 6, Nov./Dec. 1989 pp. 18–23.

Soane, David S. et al., "Polymers in Microelectronics Fundamentals and Applications," *Elesevier*, 1989, pp. 77–124.

Rutter, Edward W., et al., "A Photodefinable Benzocyclobutene Resin for Thin Film Microelectronic Applications," *Proceedings of the 1992 International Conference on Multichip Modules*, Apr. 1–3, 1992, pp. 394–400.

Mercer F. W., "Aromatic Polyther imide oxadiazoles," *High Performance Polymers*, vol. 4, No. 2, 1992 pp. 73–80.

Ahne, Hellmut, "Recent Advances in Photosensitive Polyamides," *Polymers for Advanced Technologies*, vol. 4, Oct. 1992, pp. 217–233.

Katsarava, R.D. et al., "Synthesis of Polyamides using Activated bis-N-Oxysuccinimide Esters of Dicarboxylic Acids," *Polymer Science U.S.S.R.*, vol. 26, No. 7, 1984, pp. 1668–1678.

Konig, Wolfgang, et al., "N–Hydroxyverbindungen als Katalysatoren für die Aminolyse aktivierter Ester," *Chem. Ber.*, 106, (1973) pp. 3626–3635.

Chemical Abstracts, vol. 82 (1975), No. 58354c.
Chemical Abstracts, vol. 83 (1975), No. 43323p.
Chemical Abstracts, vol. 84 (1976), No. 151032x.
Chemical Abstracts, vol. 92 (1980), No. 181056r.
Chemical Abstracts, vol. 92 (1980), No. 215344a.

*Advanced Organic Chemistry*, Jerry March; Second Ed., McGraw-Hill Book Co., pp. 364, 376, 384 and 388 (1977).

*Primary Examiner*—Johann Richter
*Assistant Examiner*—Jane C. Osweck
*Attorney, Agent, or Firm*—Kenyon & Kenyon

[57] ABSTRACT

The dicarboxylic acid derivatives according to the invention have the following structure

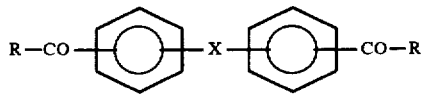

wherein X denotes O, S, $(CF_2)_m$, $C(CF_3)_2$ or $CF_2-CF(CF_3)$ (m=1 to 10), and R stems from the following compounds: fluoro- or trifluoromethyl- and nitro- or cyanophenols, thiophenols or -aminobenzenes, 4-hydroxy-, 4-mercapto- or 4-aminocoumarins, N-hydroxysuccinimides or N-hydroxymaleimides, 2-hydroxy- or 2-mercaptobenzoxazoles or -benzothiazoles and 1-hydroxy- or 1-mercaptobenzotriazoles.

3 Claims, No Drawings

DICARBOXYLIC ACID DERIVATIVES

FIELD OF THE INVENTION

The invention relates to novel dicarboxylic acid derivatives, namely diesters, dithioesters and di-amides.

BACKGROUND OF THE INVENTION

In microelectronics, highly heat-resistant polymers are needed, particularly as protective and insulating coatings and as dielectrics (in this regard, see, for example, SAMPE Journal, vol. 25 (1989), No. 6, pages 18 to 23, and Proceedings of the 1992 International Conference on Multichip Modules, pages 394 to 400). Some of the polymers used, for example the homopolymers and copolymers of aromatic polyethers and the precursors of polyimides (PI) and polybenzoxazoles (PBO), exhibit good solubility in organic solvents and good film-forming properties and thus can be applied to electronic components by the spin-coating technique (see, for example, High-Performance Polymers, vol. 4 (1992), No. 2, pages 73 to 80, and Polymers for Advanced Technologies, vol. 4 (1993), pages 217 to 233).

Heat treatment causes such polymer precursors to undergo cyclization, namely it converts them into the corresponding polymers (PI or PBO) and confers to them their final properties. In other words, cyclization causes the disappearance of the hydrophilic groups of the poly-o-hydroxyamide, namely the NH—, OH— and CO— groups which would exert a negative effect on dielectric properties and water absorption. In this respect, the polybenzoxazoles have a decided advantage over the polyimides (which have two CO groups per imide unit) and, in particular, over the hydroxypolyimides (which have two CO groups and one OH group per imide unit). Moreover, cyclization is important in that it confers to the end product not only good dielectric properties and low water absorption, but also high heat stability.

PI and PBO precursors can, for example by addition of appropriate photoactive components, be rendered photosensitive and thus be imaged directly, namely without an auxiliary resist. This is significant, because direct imaging offers considerable cost advantages over indirect imaging.

Photosensitive PBO precursors, unlike most photosensitive PI precursors, offer the advantages of positive imaging such as lower defect density in the structuring of via holes, because, compared to negative-working systems, only a fraction of the surface is exposed to light. Moreover, when alkali-soluble PBO precursors are used, aqueous alkaline development becomes possible. Following photoimaging, the precursor is cyclized by heating.

PBO precursors that can be developed by aqueous alkali are known (see European Patent [EP] 0 023 662, European Unexamined Patent Application [EP-OS] 0 264 678 and EP 0 291 779). The photolithographic process used for this purpose is, with the exception of the cyclization, the same as in the imaging of known positive-working photoresists based on novolaks and quinone azides, a process used worldwide in numerous manufacturing lines (see, for example, D. S. Soane and Z. Martynenko, "Polymers in Microelectronics—Fundamentals and Applications", Elsevier, Amsterdam 1989, pages 77 to 124).

The alkali solubility of the PBO precursors is an important prerequisite for their use as base polymers for photosensitive dielectrics that can be developed with aqueous alkali. For microelectronic applications, the precursors must be soluble in metal ion-free developers, so that such developers can also be used for photoimaging. Developers containing metal ions can have an adverse effect on the electric function of the components.

The most current method for making alkali-soluble PBO precursors, namely poly-o-hydroxyamides, is the reaction of a dicarboxylic acid chloride and an appropriate bis-o-aminophenol. A soluble base such as pyridine is usually employed to absorb the hydrogen chloride formed during the reaction (see EP-OS 0 264 678 and EP 0 291 779). Although this method affords precursors soluble in metal ion-free aqueous alkaline developers, it has the drawback that chloride ions remain in the polymer. Such a polymer is unusable as coating material for microelectronic components, because the chloride ions cause corrosion and can thus exert a strong adverse affect on the function of said components. For this reason, it is necessary to purify the polymer by means of ion exchangers. This purification, however, is tedious and expensive, because it involves additional processing steps, such as preparing the ion exchange column, dissolving the polymer, passing the solution through the column followed by washing and then, once again, precipitation and drying.

A requirement for the preparation of poly-o-hydroxyamides is that the dicarboxylic acid chloride must react predominantly with the amino groups of the bis-o-aminophenol (with amide formation) and not with its hydroxyl groups (with ester formation), namely the selectivity of the reaction for amide formation must be very high. If ester formation cannot be prevented or strongly suppressed, insufficiently alkali-soluble polymers are obtained. Low reaction selectivity can also cause gel formation in the polymer solution which would render the resulting poly-o-hydroxyamide unfiltrable and thus unusable.

Processes for chloride-free synthesis of poly-o-hydroxyamides and poly-o-mercaptoamides have also been described. Thus it is known from EP-OS 0 158 726 to react a dihydroxy- or dimercaptodiamino compound with a dicarboxylic acid in the presence of a carbodiimide. In this reaction, urea residues formed by a rearrangement reaction remain on the resin, and this often cause problems. Such residues have an adverse effect on the thermal stability of the polybenzoxazole or polybenzothiazole and on the quality of the coatings prepared therefrom. Moreover, the polymers prepared by this process are not sufficiently soluble in metal ion-free aqueous alkaline developers.

An alternative chloride-free method of preparation of poly-o-hydroxyamides involves using a condensing agent such as 1-ethoxycarbonyl-2-ethoxy-1,2- dihydroquinoline and 1,1'-carbonyldioxydi-1,2,3-benzotriazole in the reaction of the dicarboxylic acid with bis-o-aminophenol (see EP-OS 0 391 196). The polymers prepared in this manner, however, also show insufficient solubility in metal ion-free aqueous alkaline developers.

Processes in which phosphorus compounds are used to form amides are also known (see EP-OS 0 481 402, U.S. Pat. No. 4 331 592 and DE-OS 37 16 629). In the case of poly-o-hydroxyamides, however, such syntheses afford cyclized, i.e. alkali-insoluble products, or else phosphorus-containing, partly chemically bound residues remain in the polymer which, because of the doping ability of phosphorus thus becomes unusable for microelectronic applications. In contrast to ionic impurities, such residues cannot be removed, for example, with ion exchangers.

In addition to being adequately soluble in metal ion-free aqueous alkaline developers, precursors of polybenzoxazole and polybenzothiazole must also be sufficiently soluble in various nontoxic organic solvents. The solubility in organic solvents can be improved, for example, by acetylation of the hydroxyl groups (see EP-OS 0 264 678), but this at the same time also reduces the solubility in alkaline developers.

SUMMARY OF THE INVENTION

The object of the invention is to provide dicarboxylic acid derivatives allowing the preparation of poly-o-hydroxyamides and poly-o-mercaptoamides with high solubility both in metal ion-free aqueous alkaline developers and in nontoxic organic solvents.

According to the invention, this objective is reached by means of dicarboxylic acid derivatives having the structure:

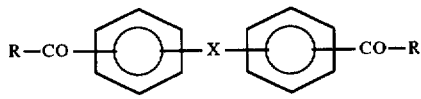

wherein

X=O, S, $(CF_2)_m$, $C(CF_3)_2$ or $CF_2-CF(CF_3)$, and m=1 to 10;

R is

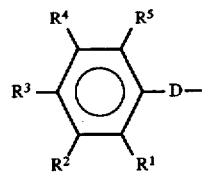

wherein

D is O, S or NH, and $R^1$, $R^2$, $R^3$, $R^4$, $R^5$ are independently H, F, $CH_3$ or $CF_3$ with the proviso that at least one of groups $R^1$ to $R^5$ is F or $CF_3$ and at the most two of groups $R^1$ to $R^5$ are $CH_3$ or $CF_3$;

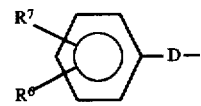

where

D is O, S or NH, and $R^6$, $R^7$ are independently H, F, $CH_3$, $CF_3$, CN or $NO_2$ with the proviso that at least one of groups $R^6$ and $R^7$ is CN or $NO_2$;

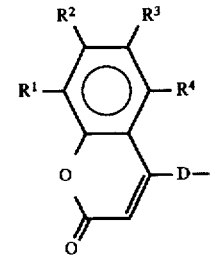

wherein

D is O, S or NH, and $R^1$, $R^2$, $R^3$, $R^4$ are independently H, F, $CH_3$ or $CF_3$, with the proviso that at the most two of groups $R^1$ to $R^4$ are $CH_3$ or $CF_3$;

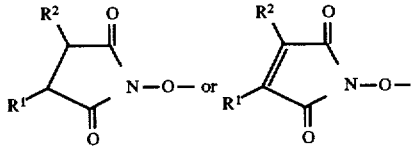

wherein $R^1$ and $R^2$ are independently H, F, $CH_3$ or $CF_3$;

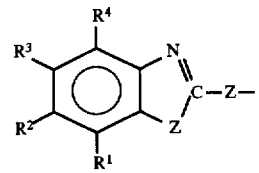

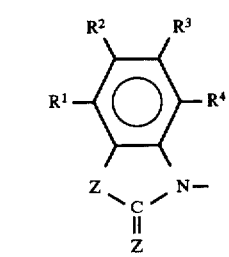

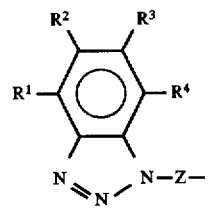

wherein

Z=O or S, and $R^1$, $R^2$, $R^3$, $R^4$ are independently H, F, $CH_3$ or $CF_3$ with the proviso that at the most two of groups $R^1$ to $R^4$ are $CH_3$ or $CF_3$.

DETAILED DESCRIPTION OF THE INVENTION

The dicarboxylic acid derivatives according to the invention are diesters, dithioesters and diamides, namely active acid derivatives. These active esters, thioesters and amides stem from the following compounds: fluoro- or trifluoromethyl- and nitro- or cyanophenols, -thiophenols or -aminobenzenes, 4-hydroxy-, 4-mercapto- and 4-aminocoumarins, N-hydroxysuccinimides and N-hydroxymaleimides, 2-hydroxy and 2-mercaptobenzoxazoles or -benzothiazoles as well as 1-hydroxy- and 1-mercaptobenzotriazoles. Because of these components, the dicarboxylic acid derivatives according to the invention exhibit selective reactivity in the reaction with bis-o-aminophenols or bis-o-aminothiophenols, in that amide and not ester formation takes place.

Active esters, for example those based on amino acids, are known [see DE-OS 22 63 502 and Chem. Ber. 106, 3626–3635 (1973)] as are those of aliphatic dicarboxylic acids and isophthalic acid [see Polymer Sci. USSR, 26, No. 7, 1668–1678)]. Dicarboxylic acid-based active esters as prepared according to the invention, however, have thus far not been described.

The active dicarboxylic acid derivatives according to the invention are characterized by the fact that two aromatic rings in the acid component are linked by a special bridge, namely by one of the following groups: —O—, —S—, —(CF$_2$)$_m$—, —C(CF$_3$)$_2$ or —CF$_2$—CF(CF$_3$)—.

The advantage of these flexible bridges is that they have a solubility-enhancing effect. Moreover, they also improve adhesion, storage stability and UV transparency. Other bridges, such as —CH$_2$— and —CO—, too, can improve solubility, but they also have a deleterious effect on other properties, such as heat stability or UV transparency.

A particularly well-suited bridge is the —O— group, for example in diphenyl ether 4,4'-dicarboxylic acid. The following active esters according to the invention are therefore especially well suited:

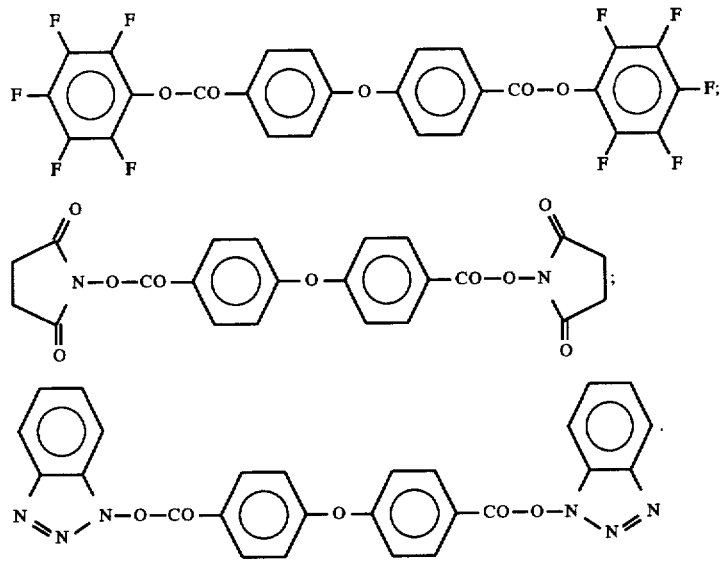

Advantageously, the dicarboxylic acid derivatives according to the invention are prepared by reaction of a dicarboxylic acid having the structure

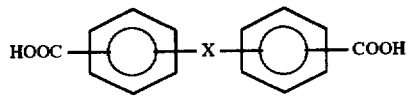

and a compound having the structure

R—H in the presence of a carbodiimide, preferably dicyclohexylcarbodiimide. Groups X and R have the same meaning as indicated hereinabove. The hydrogen atom in compound RH is attached to an atom of oxygen, sulfur or nitrogen and, hence, is an "active" hydrogen atom.

The dicarboxylic acid derivatives, however, can also be prepared by reaction of an RH compound and a dicarboxylic acid chloride. In this case, the reaction products can be adequately purified in simple fashion by recrystallization.

The active dicarboxylic acid derivatives according to the invention make it possible to prepare polybenzoxazole and polybenzothiazole precursors with exclusion of impurities such as chloride ions and metal ions or phosphorus compounds, which have a deleterious effect on electronic components. The reaction with a bis-o-aminophenol or bis-o-aminothiophenol is preferably carried out in the presence of a basic catalyst, particularly a tertiary amine such as pyridine or triethylamine. The precursors thus prepared are readily soluble in metal ion-free aqueous alkaline developers, namely the selectivity of the reaction for amide formation is sufficient, so that said precursors are suitable as base resins for photosensitive dielectrics. Moreover, the precursors are readily soluble in a number of organic solvents.

The invention will now be further illustrated by way of the following non-limiting examples.

EXAMPLE 1

Preparation of a Diester from Diphenyl Ether 4,4'-Dicarboxylic Acid and Pentafluorophenol In a 1-liter 3-necked flask, 20.0 g (77.5 mmol) of diphenyl ether 4,4'-dicarboxylic acid and 28.5 g (155 mol) of pentafluorophenol were dissolved in 270 mL of dry N-methylpyrrolidone under nitrogen (protective gas) and with agitation. The resulting solution was cooled to −15° C. and to it was added slowly and dropwise a solution of 32.0 g (155 mmol) of dicyclohexylcarbodiimide in 175 mL of N-methylpyrrolidone. At the end of the addition, the reaction solution was allowed to agitate first 2 h at about −15° C., then 14 h at about 23° C. and finally 5 h at about 50° C. After cooling to room temperature, the reaction solution was allowed to stand about 18 to 20 hours. The precipitate (dicyclohexylurea) was filtered off, and the clear reaction solution was added dropwise to 1600 mL of water with vigorous agitation. The solid precipitate was filtered off, washed three times with 50-mL portions of water and then treated with 500 mL of isopropanol. The mixture was allowed to agitate about 20 hours. It was then filtered, and the filter cake was washed three times with 50-mL portions of isopropanol. The material was then dried at 30° C., first 24 h at about 20 mbar and then 48 h at about 2 mbar. The diester thus obtained (yield: 28 g) melted at 175° C.

EXAMPLE 2

Preparation of a Diester from Diphenyl Ether 4,4'-Dicarboxylic Acid and N-Hydroxysuccinimide In a 1-liter 3-necked flask, 30.0 g (116.1 mmol) of diphenyl ether 4,4'-dicarboxylic acid and 26.7 g (232.2 mmol) of N-hydroxysuccinimide were dissolved in 310 mL of dry N-methylpyrrolidone under nitrogen (protective gas) and with agitation. The resulting solution was cooled to −15° C. and to it was added slowly and dropwise a solution of 47.9 g (232.2 mmol) of dicyclohexylcarbodiimide in 265 mL of N-methylpyrrolidone. At the end of the addition, the reaction solution was allowed to agitate first 2 h at about −15° C., then 24 h at about 23° C. and finally 6 h at about 80° C. After cooling to room temperature, the reaction solution was allowed to stand about 18 to 20 hours. The precipitate (dicyclohexylurea) was filtered off, and the clear reaction solution was added dropwise and with vigorous agitation to 3000 mL of a mixture of 3 parts of water and 1 part of acetic acid. The solid precipitate was filtered off and washed three times with 50-mL portions of water. It was then stirred, first for 24 h in 500 mL of ethyl acetate and then for 18 to 20 h in 500 mL of isopropanol. The mixture was then filtered, and the filter cake was washed three times with 50-mL portions of isopropanol. The material was dried at 30° C., first 24 h at about 20 mbar and then 48 h at about 2 mbar. The diester thus obtained (yield: 34 g) melted at 185° C.

EXAMPLE 3

Preparation of a Diester from Diphenyl Ether 4,4'-Dicarboxylic Acid and 1-Hydroxybenzotriazole In a 4-liter 3-necked flask, 204 g (0.79 mol) of diphenyl ether 4,4'-dicarboxylic acid and 268 g (1.984 mol) of 1-hydroxybenzotriazole were dissolved in 800 mL of dry N-methylpyrrolidone under nitrogen (protective gas) and with agitation. To this solution was added dropwise, with ice cooling and over a period of 3 hrs, a solution of 456 g (2.21 mol) of dicyclohexylcarbodiimide in 800 mL of N-methylpyrrolidone (temperature about 0° C.). At the end of the addition, the reaction solution was allowed to agitate 2 h at about 0° C. after which an additional 800 mL of N-methylpyrrolidone was added and the solution was allowed to stand 20 h at about 23° C. The reaction solution was again cooled to about 0° C. The precipitate (dicyclohexylurea) was filtered off and washed four times with 100-mL portions of cold N-methylpyrrolidone. The clear filtrate was diluted with N-methylpyrrolidone to a total of 4 L, and then 800 mL of distilled water was slowly added dropwise with vigorous agitation. The resulting precipitate was filtered off, washed four times with 200-mL portions of isopropanol and then suspended in 1500 mL of isopropanol. The mixture was heated at reflux for 15 min, cooled to room temperature and filtered. The solid was dried at 30° C., first 24 h at about 20 mbar and then 48 h at about 2 mbar. The diester thus prepared (yield: 175 g) melted at 198° C.

We claim:

1. A process for making a dicarboxylic acid compound having the structure:

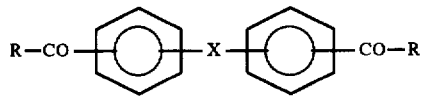

wherein $X=O, S, (CF_2)_m, C(CF_3)_2$ or $CF_2—CF(CF_3)$, and $m=1$ to 10;

R is

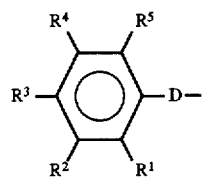

wherein

D is O, S or NH, and $R^1$, $R^2$, $R^3$, $R^4$, $R^5$ are independently H, F, $CH_3$ or $CF_3$ with the proviso that at least one of groups $R^1$ to $R^5$ is F or $CF_3$ and at the most two of groups $R^1$ to $R^5$ are $CH_3$ or $CF_3$;

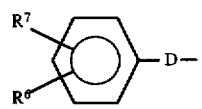

where

D is O, S or NH, and $R^6$, $R^7$ are independently H, F, $CH_3$, $CF_3$, CN or $NO_2$ with the proviso that at least one of groups $R^6$ and $R^7$ is CN or $NO_2$;

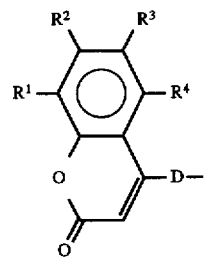

wherein

D is O, S or NH, and $R^1$, $R^2$, $R^3$, $R^4$ are independently H, F, $CH_3$ or $CF_3$, with the proviso that at the most two of groups $R^1$ to $R^4$ are $CH_3$ or $CF_3$;

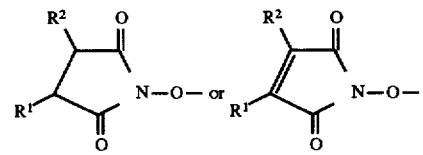

wherein $R^1$ and $R^2$ are independently H, F, $CH_3$ or $CF_3$;

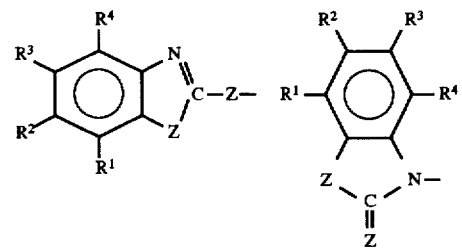

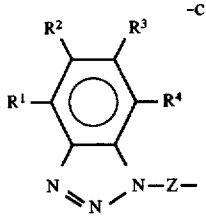

wherein

Z=O or S, and $R^1$, $R^2$, $R^3$, $R^4$ are independently H, F, $CH_3$ or $CF_3$ with the proviso that at the most two of groups $R^1$ to $R^4$ are $CH_3$ or $CF_3$, comprising reacting a dicarboxylic acid having the structure

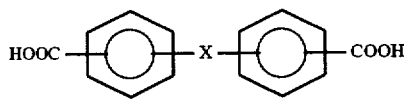

with a compound having the structure

R—H in the presence of a carbodiimide.

2. The process according to claim 1, wherein the reaction is carried out in the presence of dicyclohexylcarbodiimide.

3. A process for making poly-o-hydroxyamides and poly-o-mercaptoamides comprising reacting a dicarboxylic acid compound with a bis-o-aminophenol or bis-o-aminothiophenol, said dicarboxylic acid compound having the structure:

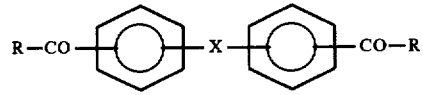

wherein

X=O,S, $(CF_2)_m$, $C(CF_3)_2$ or $CF_2$—$CF(CF_3)$, and m=1 to 10;

R is wherein

D is O, S or NH, and $R^1$, $R^2$, $R^3$, $R^4$, $R^5$ are independently H, F, $CH_3$ or $CF_3$ with the proviso that at least one of groups $R^1$ to $R^5$ is F or $CF_3$ and at the most two of groups $R^1$ to $R^5$ are $CH_3$ or $CF_3$;

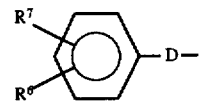

where

D is O, S or NH, and $R^6$, $R^7$ are independently H, F, $CH_3$, $CF_3$, CN or $NO_2$ with the proviso that at least one of groups $R^6$ and $R^7$ is CN or $NO_2$;

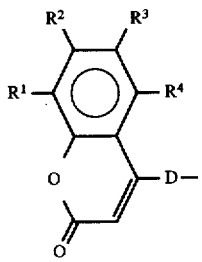

wherein

D is O, S or NH, and $R^1$, $R^2$, $R^3$, $R^4$ are independently H, F, $CH_3$ or $CF_3$, with the proviso that at the most two of groups $R^1$ to $R^4$ are $CH_3$ or $CF_3$;

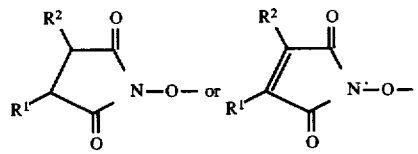

wherein $R^1$ and $R^2$ are independently H, F, $CH_3$ or $CF_3$;

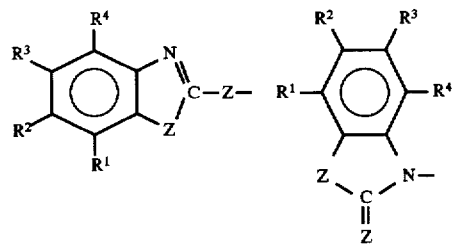

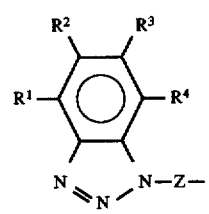

wherein

Z=O or S, and $R^1$, $R^2$, $R^3$, $R^4$ are independently H, F, $CH_3$ or $CF_3$ with the proviso that at the most two of groups $R^1$ to $R^4$ are $CH_3$ or $CF_3$.

* * * * *